United States Patent [19]
Grim

[11] Patent Number: 5,632,723
[45] Date of Patent: *May 27, 1997

[54] CUSTOM IN SITU FORMABLE BRACE

[75] Inventor: Tracy E. Grim, Broken Arrow, Okla.

[73] Assignee: Royce Medical Company, Camarillo, Calif.

[*] Notice: The term of this patent shall not extend beyond the expiration date of Pat. No. 5,437,614.

[21] Appl. No.: 459,463

[22] Filed: Jun. 2, 1995

Related U.S. Application Data

[62] Division of Ser. No. 17,817, Feb. 16, 1993, Pat. No. 5,437,614.

[51] Int. Cl.$^6$ ........................................... A61F 5/02
[52] U.S. Cl. ..................... 602/19; 602/6; 602/8
[58] Field of Search ............. 602/6, 8, 19, 14; 2/44; 128/95.1, 99.1

[56] References Cited

U.S. PATENT DOCUMENTS

| | | |
|---|---|---|
| 443,764 | 12/1890 | Hilliard . |
| 3,667,457 | 6/1972 | Zumaglini . |
| 3,945,376 | 3/1976 | Kuehnegger . |
| 4,475,543 | 10/1984 | Brooks et al. . |
| 4,622,957 | 11/1986 | Curlee . |
| 4,628,913 | 12/1986 | Lerman . |
| 4,852,557 | 8/1989 | Grim . |
| 4,948,092 | 8/1990 | Kasper et al. . |
| 4,993,409 | 2/1991 | Grim . |
| 5,062,414 | 11/1991 | Grim . |
| 5,074,288 | 12/1991 | Miller . |
| 5,437,614 | 8/1995 | Grim . |

*Primary Examiner*—Beverly M. Flanagan
*Attorney, Agent, or Firm*—Oppenheimer Poms Smith

[57] ABSTRACT

A soft-goods type, custom "in situ" formable back brace for supporting a weakened or injured back and/or neck is disclosed having hardenable components which conform to the unique configuration of a patient's torso. An initially flexible rear torso component, generally extending circumferentially around the patient's back, is releasably coupled to the torso using a plurality of Velcro-type securing straps. Alternatively, an initially flexible front torso component in combination with a rear component may be releasably coupled to a patient's torso. Once properly secured, liquid, preferably water, may be introduced into each component to activate the activatable, hardenable material encapsulated therein. Each component may be further comprised of a plurality of panels or pads with elasticized, resilient material interposing adjacent panels. The panels or pads may be permanently or removably integrated into each torso component. Additional supporting strut members may be provided to isolate and minimize upper neck and head movement for patient's having severe neck and/or back injuries. The hardenable components may be activated by introduction of water or other suitable liquid through inlet port conduits provided on the exterior surface of each said component. Alternatively, activation of the included prepolymer impregnated matrix may be accomplished by immersing the hardenable component in liquid. An inflatable pneumatic pad may also be included on one or more component interior surfaces to provide minor fitting adjustment. Additional padding may be included on each component for the patient's comfort.

51 Claims, 6 Drawing Sheets

CUSTOM IN SITU FORMABLE BRACE

CROSS-REFERENCE TO RELATED APPLICATION

This is a divisional of application Ser. No. 08/017,817, filed Feb. 16, 1993, which issued as U.S. Pat. No. 5,437,614 on Aug. 1, 1995.

FIELD OF THE INVENTION

This invention relates generally to back supports and braces. More particularly, it relates to a custom-fit back support suitable for persons having substantial back and/or neck injuries.

BACKGROUND OF THE INVENTION

In the orthopaedic back brace or support field, numerous back support designs have been developed to provide support and minimize movement of a patient's back and neck after sustaining injuries of varying severity. U.S. Pat. No. 4,622,957, for example, discloses a therapeutic corset brace, having inflatable cells therein, which exerts a supporting force against the lower back region when properly secured. Such a brace is subject to positional shifting if not properly secured about the torso. Further, the inflatable bladders are subject to loss of air pressure resulting in a reduction of force necessary to adequately support and immobilize the injured or weakened back and/or neck. Moreover, the inflatable bladders are capable of providing only a moderate degree of customized fit; the fit being dependent upon the orientation and number of inflatable bladders.

Other back support designs, similar to that disclosed in U.S. Pat. No. 5,062,414, employ a gel-like substance contained in a flexible pouch which can be inserted into a conventional corset-like back support. The gel pad is capable of generally conforming to the shape of the lower back and spinal region, and is held in place by inflatable bladders located behind the gel pad. Upon inflation, the air bladders, in combination with the gel pad, provide only a moderate degree of custom fit.

Back supports employing high viscosity gel pads as support members inherently lack sufficient rigidity to adequately regulate and minimize back movement. These limitations result in a back support system which suffers from undesirable variations of supporting force depending on the temperature and orientation of the gel-like pads.

More conventional designs employ foam padding in combination with flexible elastic belting material strapped around the torso to minimize back movement. These traditional approaches fail to provide a sufficient degree of customized fit needed to properly minimize and regulate back and/or neck movement.

Accordingly, a principal objective of the present invention is to provide an orthopaedic custom "in situ" formable back support suitable for back and/or neck injuries of varying degrees, which is lightweight, truly and uniquely formable to a patient's torso, and is easily fitted and removed. Additional objectives are to provide a custom formable back support which is simpler to fabricate and may be custom formed "in situ" in a short period of time, as compared to conventional approaches such as those described hereinabove. In accomplishing these objectives, the invention will increase the stability of the weakened or injured back and/or neck, and ensure the prevention of undesirable movements which could further injure the back and/or neck or complicate the healing process.

SUMMARY OF THE INVENTION

In accordance with one illustrative embodiment of the present invention, a custom-fit back support is formed "in situ," or in place, with a rear soft-goods type torso component being releasably coupled to the torso; the component being formed of gas or liquid permeable material impregnated with an activatable, hardenable material which structurally conforms to the shape of the torso surface when activated. The rear component is preferably secured to the torso by at least one securing strap which may include Velcro-type material or other fastening arrangements to hold the component in place, during both activation of the hardenable material, and thereafter while the back support is in use.

In one particular embodiment of the present invention, front and rear torso components are provided, and each is comprised of a single component panel containing activatable, hardenable material. The rear torso component generally covers a significant portion of the patient's back, with lateral ends extending just beyond the sides of the torso. The front torso component generally covers a significant portion of the patient's front torso, with lateral ends extending to at least the sides of the torso. The initially flexible torso components are fitted around the torso such that the lateral ends of the rear component pass over and overlap the lateral ends of the front component generally along the sides of the torso. The front and rear torso components may be releasably coupled together and to the torso by a plurality of securing straps and fastening arrangements secured along and adjacent the lateral ends of the components. Incremental adjustment of the back support about the torso is accomplished by tightening or loosening each of the securing straps.

The securing straps extending from the lateral ends of the rear component may be secured on the front torso component using fastening arrangements attached thereon. The front torso fastening arrangements may be of a conventional type employing a buckle and loop configuration. The securing straps may alternatively be covered with Velcro-type fabric, being received and secured on Velcro-type mating fabric attached to the front component. Velcro is a trademark, and the products sold under the Velcro trademark are mating fabric pads, with one of the pads having its surface provided with a fine array of closely spaced outwardly protruding hooks, and the other mating pad having outwardly extending loops or other material with which the hooks may engage.

After being properly fitted and adjusted, a predetermined volume of water or other liquid is introduced into each hardenable component typically by coupling a liquid-filled syringe to at least one inlet port provided on each hardenable component. The water activates the activatable, hardenable material encapsulated within each component, causing the component to harden and form to the unique contour of the patient's torso configuration.

In accordance with another embodiment of the present invention, front and rear torso components are each comprised of a plurality of component panels coupled together, optionally with elasticized resilient material. Similar fastening attachments and securing straps described previously may be provided to releasably couple the front and rear torso components around the torso. Each component panel includes activatable, hardenable material which, when activated by the introduction of water or other liquid, hardens and conforms to the unique contour of the torso surface. The coupling arrangements in combination with the nowhardened component panels provides a sufficiently rigid supporting structure for the injured back, yet provides some minimal degree of expansion and contraction of the back support assembly. Such an embodiment is suitable for less severe back and neck injuries or for patients undergoing recuperative or rehabilitative physical therapy which may require some minimal back movement. In an alternative embodiment, the component panels may be removable from the torso component assemblies, and may be replaced by other component panels or replacement splints having varying degrees of rigidity.

In another embodiment of the present invention, a pneumatic pad may be removably or permanently affixed to the interior surface of each torso component, allowing for minor fitting adjustments of each component on the torso surface. Particularly if swelling is present with the initial filling, when the swelling subsides the bladder may be inflated to conform to the patient's reduced configuration. The pneumatic pad may be included on the rear torso component, but may additionally be provided on the front torso component. The pneumatic pad may be coextensive with the torso component surface or, alternatively, may encompass only a portion of each torso component. Each pneumatic pad may be pre-inflated, and may include inflation and deflation arrangements, and pressure regulation. Further, the pneumatic pad may be comprised of a single air bladder or a plurality of air bladders therein. Additional foam padding or other resilient material may cover at least one side of the pneumatic pad. The bladder may be either pre-inflated or preferably inflatable to desired levels. Reference is made to U.S. Pat. Nos. 4,948,092, and 4,993,409 for bladder inflation and control arrangements.

In accordance with yet another embodiment of the present invention, each torso component may be comprised of a molded foam supporting frame having a plurality of molded recesses into which hardenable component panels may be releasably installed and secured. Typically, Velcro-type attachment material is provided on each replaceable component panel which is removably affixed to Velcro-type mating material lining each panel recess. Each recess within the molded foam supporting frame may include at least one through-hole such that each inlet port provided on the component panels can be accessed from the exterior of the brace assembly.

After securing the component panels into the molded recesses of the foam supporting frame, vis a vis the Velcro-type attachment material, the front and rear torso component assemblies may be mounted to the torso and secured by a plurality of Velcro-type securing straps or by other conventional fastening means. A predetermined volume of water or other liquid may be introduced into each component panel through the through-hole provided for each inlet port. Upon completion of the chemical reaction, typically between 3 to 5 minutes, the component panels harden and conform to the individual's unique torso configuration. Incremental adjustment of the back support assembly can be accomplished by tightening or loosening the securing straps or by varying the inflation of pneumatic bladders.

In another embodiment of the present invention, the back support is comprised of a broad belt member extending circumferentially around the individual's lower torso. The supporting belt is preferably constructed from elastic or resilient fabric which is generally dimensioned to encircle the lower torso. A hardenable component pad may be affixed to the middle portion of the belt such that the component pad engages the lower back symmetrically about the spine when the supporting belt is securely fastened to the torso. The supporting belt may be initially mounted to the individual and secured by large Velcro pads covering the opposed ends of the belt. The component pad may be integrally secured to the supporting belt or, in a preferred embodiment, may be inserted into a pouch sewn into the supporting belt and secured therein. The pouch may be constructed of nylon or other durable material. Closed cell foam may cover the supporting belt to provide additional comfort to the patient. A layer of brushed nylon may also be included for engaging the torso surface. The component pad may include an inlet port through which water is introduced to activate the encapsulated activatable, hardenable material. Further, an outlet vent may be provided on the component pad to permit the escape of air and other gasses evolving from the chemical reaction. The outlet vent may be positioned adjacent the inlet port on the component pad.

Alternatively, the removable component pad may be immersed in water, thus activating the activatable, hardenable material, reinserted into the pouch, and forcefully pressed against the lower back region by securing the supporting belt around the torso. Upon completion of the chemical reaction, the component pad hardens and conforms to the unique contour of the individual's lower back and spine configuration. The component pad may include additional wedge-shaped foam padding to provide added support to the spinal recess area of the patient's lower back.

In one particular embodiment of the present invention, the rear torso assembly is comprised of an upper component and a lower component. The lower component extends generally horizontally along the lower back, and is mounted on a main belt member which encircles the lower torso. Velcro-type mating material preferably covers at least the opposed ends of the main belt for securing the lower component to the patient's lower back. A pair of support struts are mounted to the lower component, extend along opposite sides of the spine, and are mounted to the upper component which extends generally horizontally just below the shoulder joints.

The upper component is mounted to an upper component belt which encircles the upper torso and is secured to the upper back preferably by Velcro mating material covering at least the opposed ends of the upper component belt. The upper ends of the support struts extend beyond the upper component and terminate near the top of the patient's shoulders, with each strut angling away from the spine and generally toward the direction of the shoulder joints.

The support struts may be constructed of aluminum or high-strength engineering plastics or composites. Additionally, reinforcement plates, constructed of aluminum or other suitable materials, may be included at the mounting sites of the support struts and the upper and lower components. The reinforcement plates may have width and thickness dimensions similar to those of the support struts, or may have different dimensions. A plurality of rivets or other fasteners may be used to secure the upper and lower components to the supporting struts. Additional reinforcement plates may be included on either side of each component mounting site to help distribute the force of the rivets against the component surfaces. A layer of closed cell foam and brushed nylon may cover at least the upper and lower component surfaces for engaging the torso. Alternatively, the foam and brushed nylon layers may be laminated, and may be formed to include molded recesses to accommodate the reinforcement plates and rivet ends. In addition to the upper component belt and the main component belt, additional securing straps may be attached to each supporting strut, extend circumferentially around the torso, and secured near the center of the chest by Velcro mating material covering the straps. The securing straps may include foam padding affixed thereon, providing comfort for the patient.

In a preferred embodiment, the upper component belt and additional securing straps fastened to each supporting strut may extend circumferentially around the torso and terminate on a front apron assembly generally dimensioned to cover the middle chest and upper abdominal region of the front torso. The apron assembly may include a plurality of Velcro-covered straps and/or pads or other arrangements to receive the securing straps fastened to the pair of rear struts. The apron assembly preferably includes an apron component containing activatable, hardenable material which may be sewn into the apron assembly structure or, alternatively, may be removably inserted into a receiving pouch provided thereon. The hardenable apron component may include at least one inlet port for introducing water into the included activatable, hardenable material. Alternatively, the apron component may be removed from the apron assembly, immersed in water to activate the hardenable material, reinserted into the apron pouch, and secured against the front torso by use of the securing straps.

In accordance with yet another embodiment of the present invention, a single formable component of moderately complex geometry comprises the entirety of the rear torso component. The one-piece rear component extends generally from the lower back to the shoulder area, with the main body of the brace being oriented along the patient's spine. The brace is formed to include a pair of upper, lower, and shoulder protrusions which symmetrically extend horizontally outward from the main body of the brace. The upper protrusions extend toward the sides of the torso just below the shoulder joints, while the lower protrusions extend generally along the waist line of the lower back. An oblong shaped cut-out through the mid-spine region of the brace provides a minimum of spinal movement.

The upper portion of the brace includes a pair of shoulder protrusions which extend upward along the spine angling generally toward the shoulder joints. A pair of securing straps extend from fastening arrangements preferably positioned just above the upper protrusions, under and around each shoulder, and terminate on receiving arrangements provided on the upper ends of the pair of shoulder protrusions. The body of the brace is coupled to the torso by a plurality of securing straps fastened to the outward ends of the lower and upper protrusions respectively, and extending circumferentially around the sides and front of the torso, wherein the ends of each pair of straps overlap with Velcro mating material securing said strap ends, or alternatively may be coupled to an apron type structure. The securing straps may be fastened to the protrusion ends by conventional buckle and loop arrangements, or other fastening means. The securing straps may include foam padding integrally or removably coupled to each strap.

A plurality of inlet ports are distributed over the formable brace for introducing water to the activatable, hardenable material enclosed therein. After securing the brace to the patient, a predetermined volume of water is introduced into the formable brace which activates the encapsulated activatable hardenable material. The brace, after completion of the chemical reaction, thus conforms to the unique geometry of the patient's back. It should be noted that an apron component, as previously described hereinabove, may be used in conjunction with this and other embodiments of the present invention.

In yet another embodiment of the present invention, the front and rear torso component assemblies may include a plurality of substantially rigid upright struts adapted to immobilize a broken or severally injured neck. The upright struts may be made of aluminum, engineering plastics, or other substantially rigid material or composites. In a preferred embodiment, a pair of upright struts are secured to the rear torso component, and extend upward along opposite sides of the spine. The upper ends of the upright struts are angled generally toward the base of the skull and are fitted with component pads which engage the base of the skull, generally near the location where the spine and the skull meet. The component pads may include activatable, hardenable material which, when activated with liquid, harden and conform to the unique shape of the contact points at the base of the skull.

A single upright strut is preferably mounted to the front torso component, extending generally parallel to the sternum, and terminating at a point adjacent the patient's jaw. A chin support extends from the upper end of the front upright strut and engages the patient's chin. The chin support may be fashioned from metal wire, or molded from plastic or other moldable material. Each of the component pads and the chin support may include an additional layer of foam padding for the patient's comfort. A substantially rigid band of high-strength plastic or aluminum extends between both skull pads. The front upright strut is preferably connected to each rear upright strut by a substantially rigid band of plastic or aluminum fastened to the chin support, extending generally circumferentially around the patient's jaw, and fastened to each rear upright strut just below the skull pads.

In accordance with another aspect of the present invention, a formable jaw component may be employed to prevent or substantially minimize jaw and skull movement. The jaw component preferably encompasses the entire lower jaw and chin surfaces. At least one inlet port is provided on the jaw component through which water may be introduced to activate the hardenable material encapsulated therein. When activated, the jaw component hardens and conforms to the unique shape of the patient's lower jaw and chin.

Other objects, features, and advantages of the invention will become apparent from a consideration of the following detailed description and from the accompanying drawings.

DETAILED DESCRIPTION OF THE PREFERRED EMBODIMENTS

Figures 1, 2, 3:
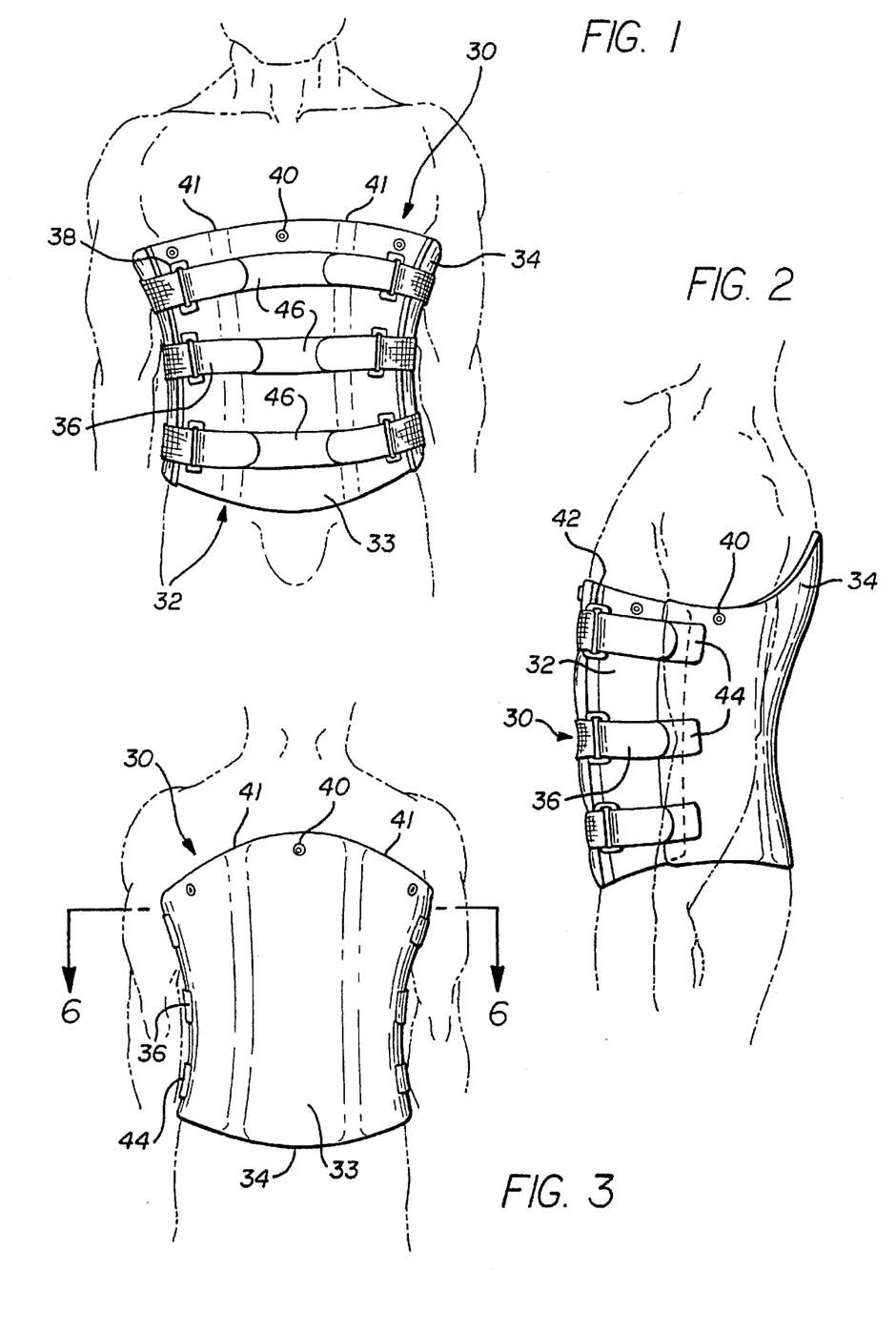
FIG. 1 is a frontal view of a custom in situ formable back brace as fitted on the patient's torso.
FIG. 2 is a side view of an embodiment of the present invention.
FIG. 3 is a rear view of a custom formable back brace as fitted on the patient's torso.

Referring more particularly to the drawings, FIG. 1 shows formable back brace 30 as it is used to support and stabilize the patient's back. FIG. 1 provides a frontal view of back brace 30 with front component 32 and rear component 34 releasably coupled to the patient's torso and secured by a plurality of securing straps 36. The lateral ends of rear component 34 preferably overlap the lateral ends of front component 32 while being incrementally tightened about the wearer's torso using straps 36 passing through buckle-loops 38 affixed to front component 32. Resilient material 41 interposing adjacent front and rear component panels 33 may provide some flexibility of the brace 30 and a high degree of custom fit about the wearer's torso. Securing straps 36 preferably include Velcro-type mating material allowing for incremental adjustment of the front and rear components 32 and 34 respectively about the torso.

As further illustrated in FIG. 1, inlet ports 40 are provided on the exterior surfaces of front and rear components 32 and 34. A liquid or gas permeable material impregnated with an activatable, hardenable material is encapsulated within front and rear components 32 and 34 respectively, both of which remain pliable and moldable until liquid is added to the permeable material. A predetermined volume of water may be injected into front and rear components 32 and 34 through inlet ports 40. The liquid, typically water, activates the urethane pre-polymer matrix, which causes front and rear components 32 and 34 to harden in the conformed shape of the patient's torso upon completion of the chemical reaction.

Through the use of securing straps 36, front and rear components 32 and 34 are firmly secured to the wearer's torso so that, upon the introduction of water, the polymer hardens and takes a form or set uniquely conforming to the shape of the patient's torso. In a preferred embodiment, straps 36 are of a Velcro-covered type allowing for incremental adjustment of the constraining force of front and rear components 32 and 34 around the torso. Velcro-type receiving strips 46 are affixed to front component 32 extending between buckle assemblies 38 mounted adjacent to the lateral ends of front component 32. Securing straps 36, with one end fastened to the lateral ends of front component 32, pass through buckle assembly 38 and are received by Velcro-type receiving strips 46.

FIG. 2 shows a side view of an embodiment of the present invention incorporating an alternative securing configuration. Adjustment of the constraining force of brace 30 around the torso is accomplished by tightening securing straps 36 through buckle loop 42. Securing straps 36 are preferably covered with Velcro-type mating material allowing for incremental adjustment of overlapping front and rear components 32 and 34 respectively.

A rear view of a back brace 30 is provided in FIG. 3. A plurality of component panels 33 comprise rear component 34 with resilient material 41 interposing adjacent component panels 33. Inlet ports 40 are provided on the exterior surface of each component panel 33 allowing for introduction of liquid to activate the encapsulated hardenable material. Component panels 33 may be permanently integrated into rear component 34. Alternatively, component panels 33 may be removable, allowing for re-installation of replacement component panels 33 or other structural members of varying rigidity. A plurality of securing straps 36 are fastened adjacent and along the lateral ends of rear component 34 at attachment sites 44.

Figure 4:
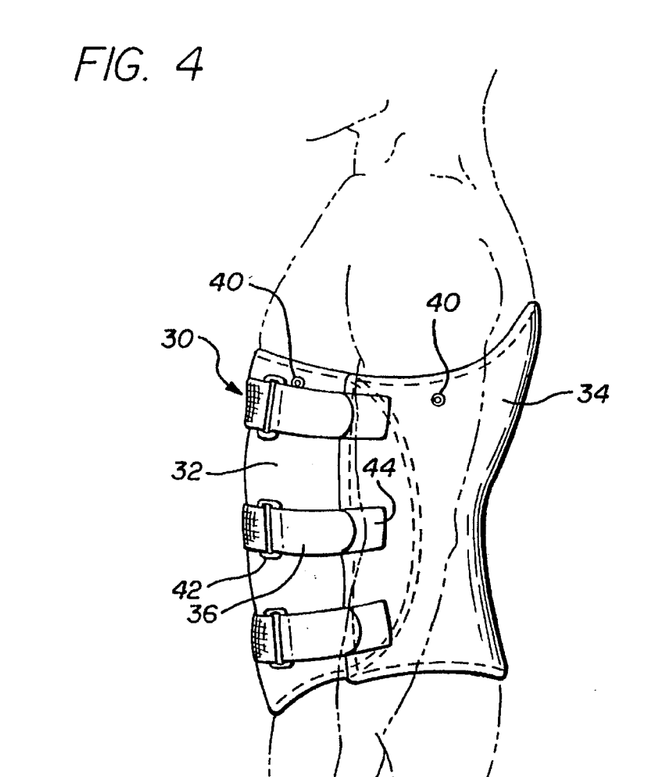
FIG. 4 is a side view of an embodiment of the invention.

An alternative embodiment of the present invention is illustrated in FIG. 4. Front and rear components 32 and 34 respectively may each be comprised of a single component panel as illustrated in FIG. 4, rather than a plurality of component panels. A plurality of inlet ports 40 are provided on the exterior surfaces of front and rear components 32 and 34 through which water may be introduced into each component to activate the activatable, hardenable material contained therein. The initially pliable front and rear components 32 and 34 are respectively coupled to the patient's torso with the lateral ends of rear component 34 preferably overlapping those of front component 32. Securing straps 36, passing through buckle loops 42, may be tightened to provide a customized and comfortable fit. Once properly secured, water or other activating liquid is introduced into front and rear components 32 and 34 through a plurality of inlet ports 40. The liquid is transported throughout the interior of front and rear components 32 and 34 thus activating the activatable, hardenable material encapsulated therein. The water activates the urethane pre-polymer which causes front and rear components 32 and 34 to harden and conform to the unique configuration of the patient's torso, thus providing a custom, in situ formed back support.

Figure 5:
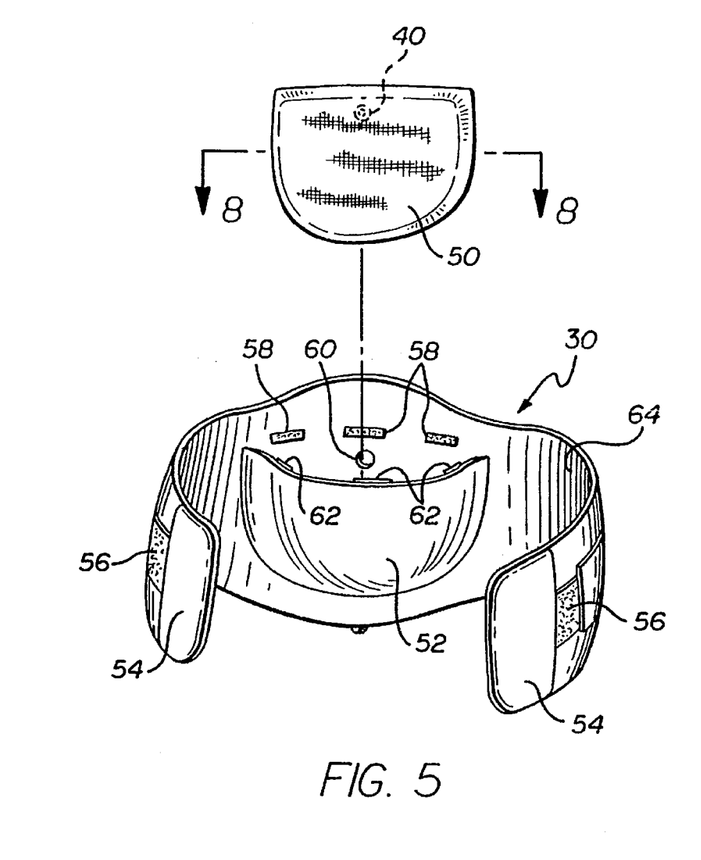
FIG. 5 is a view of an embodiment of the present invention showing a removable component pad.

Turning now to FIG. 5, this figure provides a view of an alternative embodiment of the present invention incorporating a formable component pad 50 into a supporting brace 30 preferably constructed from elasticized or resilient fabric generally dimensioned to encircle the lower torso. Component pad 50 is secured in component pouch 52 by a plurality of Velcro-type securing tabs 58 releasably coupled with corresponding Velcro-type receiving tabs 62 affixed along the periphery of the pouch 52 opening. Once component pad 50 is properly secured in component pouch 52, supporting belt brace 30 is positioned on the patient's lower torso such that component pad 50 engages the lower back symmetrically about the spine. Supporting belt brace 30 is securable around the torso using mating Velcro-type securing pads 54. After supporting belt brace 30 is properly secured around the patient's torso, a predetermined volume of liquid is introduced into component pad 50 through inlet port 40, accessed from the exterior of supporting belt brace 30 through port access hole 60. Alternatively, component pad 50 may be of a construction such that prior to being secured in component pouch 52, component pad 50 is immersed in liquid, preferably water, to activate the hardenable material contained therein. Immediately after being immersed in water, component pad 50 is placed and secured in component pouch 52. Supporting belt brace 30 is then secured to the patient's torso allowing component pad 50 to harden and conform to the unique shape of the lower back region, typically within 3 to 5 minutes.

Figure 6:
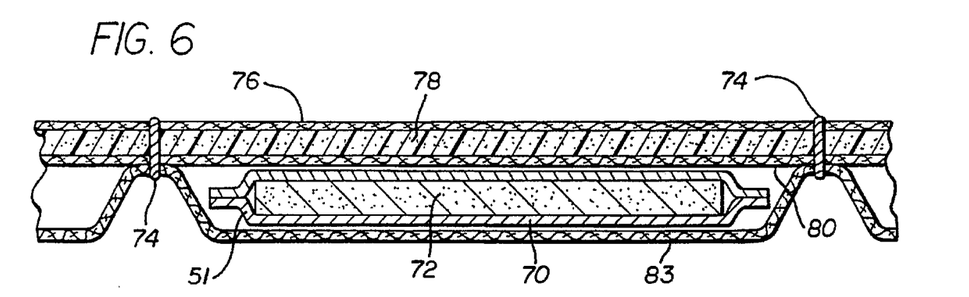
FIG. 6 is a cross-sectional view through Plain VI of FIG. 3 with a detailed showing of a component's structural configuration.

FIG. 6 is a cross-sectional view through plane VI of FIG. 3. A layer of brushed nylon 76 forms the interior, or skin-side surface, of back brace 30. A layer of foam 78 provides ample flexibility as well as cushioning. Durable shell 80, preferably constructed from durable nylon or other durable flexible material, comprises the exterior shell of front and rear components 32 and 34. Component panel 51, comprised of activatable, hardenable matrix 72 encapsulated within water impervious enclosure 70, is incorporated into brace 30 between durable shell 80 and durable exterior material 83. Each component panel 51 is properly positioned and secured between stitchings 74 bordering the periphery of each component panel 51. Component panels 51 may be permanently or removably integrated into back brace 30.

Figure 7:
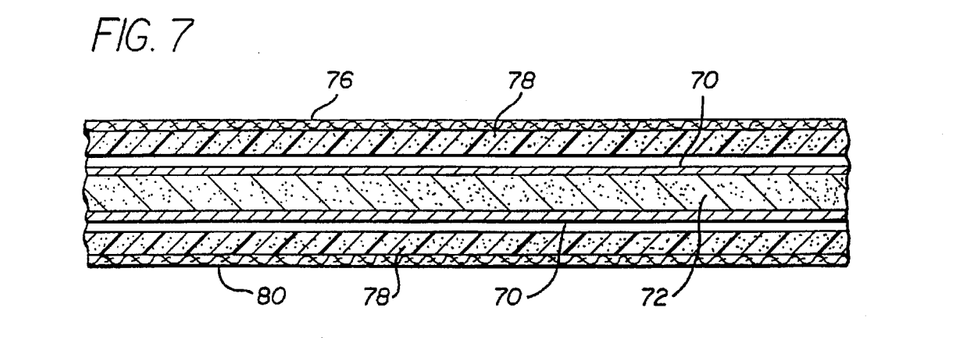
FIG. 7 is a cross-sectional view of an alternative structural configuration.

FIG. 7 illustrates a generic hardenable component construction adaptable for use in all back brace 30 configurations. Brushed nylon layer 76, cushioned by underlying closed cell foam layer 78, covers the interior surface of back brace 30 contacting the patient's skin surface. Activatable, hardenable material 72, encapsulated within water impervious enclosure 70, remains initially pliable until liquid is introduced into the matrix. An additional layer of closed cell foam 78, covered by durable shell layer 80, forms the exterior surfaces of back brace 30. Durable shell 80 may be comprised of durable nylon or other durable polymer material capable of withstanding environmental and mechanical stresses.

Figure 8:
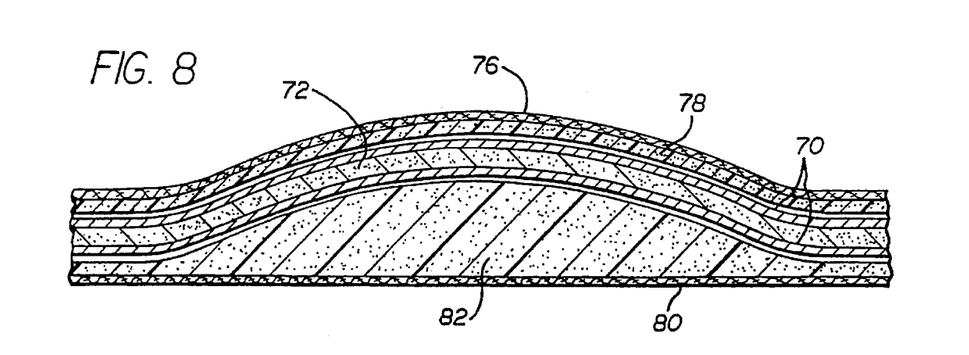
FIG. 8 is a cross-sectional view through Plain VIII of FIG. 5, illustrating a component's structure along a patient's spinal recess.

FIG. 8 is a cross-sectional view through Plane VIII of component pad 50 of FIG. 5. The component construction depicted in FIG. 8 is quite similar to that of FIG. 7, but incorporates an additional spinal recess support 82 fashioned from closed cell foam. The spinal recess support 82 may be incorporated into all back brace 30 embodiments which provides additional support to the spinal area, while inhibiting undesirable shifting of the back brace 30.

Figure 9:
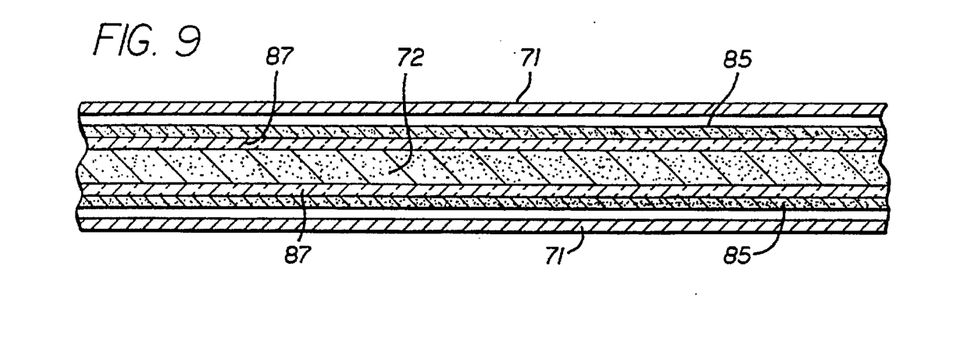
FIG. 9 is a cross-sectional view illustrating an alternative structural configuration.

FIG. 9 illustrates a cross-sectional view of an alternative component construction adaptable for use in various back brace 30 configurations. The activatable, hardenable matrix 72 may be impregnated into a layer of fiberglass fibers 87 providing additional structural rigidity. Liquid absorbent material 85, encapsulating hardenable matrix 72 and optional glass fiber layers 87, distributes water to said activatable, hardenable material 72. Liquid may be introduced into the component through inlet ports 40 (not shown) which may then be transported through liquid absorbent material 85 to permeate the hardenable matrix 72 distributed throughout the component body. Waterproof layers 71 confine the activatable materials. An additional layer of brushed nylon 76 (not shown) may be included to provide additional comfort to the patient.

Figure 10:
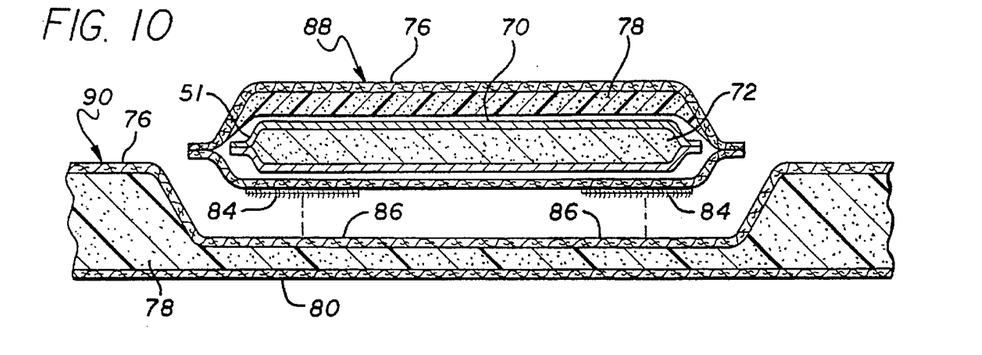
FIG. 10 is a cross-sectional view through Plain X of FIG. 11.
Figures 11, 12, 13, 14:
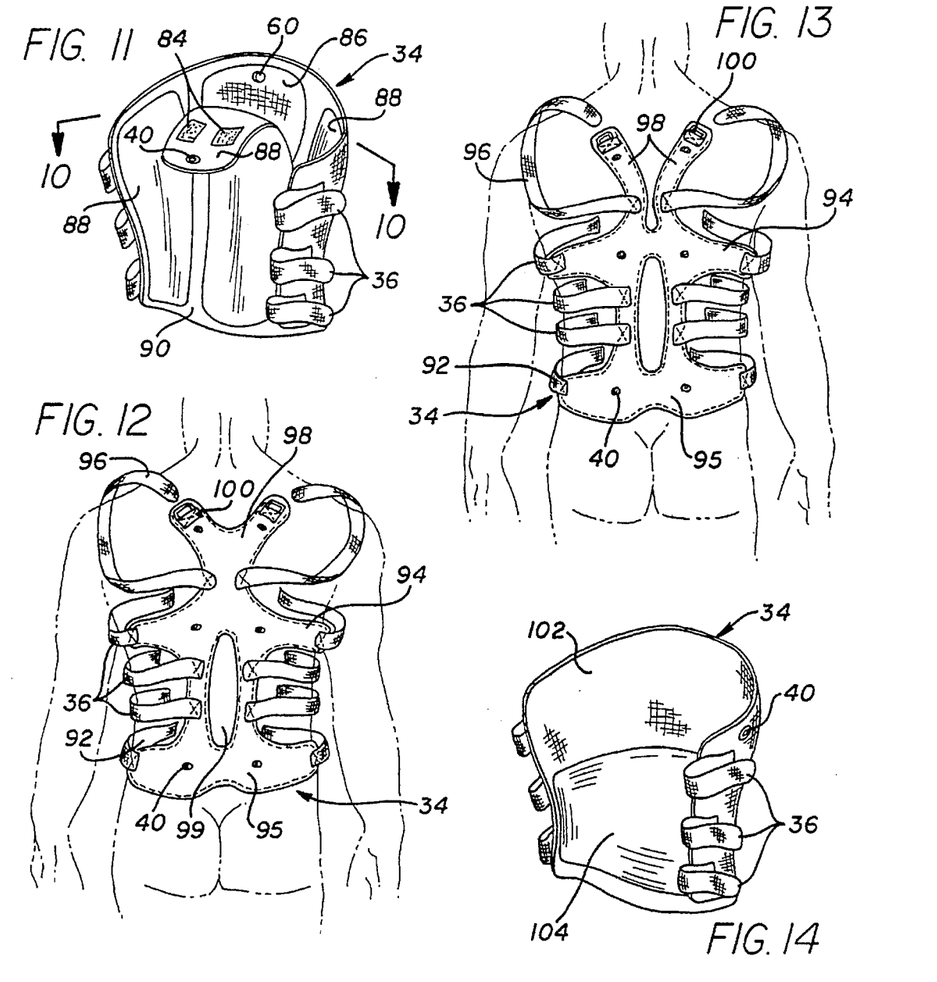
FIG. 11 is a view of an embodiment showing a plurality of detachable component panels in a molded brace frame.
FIG. 12 illustrates an embodiment of the invention used on the wearer's torso.
FIG. 13 illustrates a further embodiment of the present invention.
FIG. 14 is a view of an alternative embodiment incorporating a pneumatic pad.

A detachable panel assembly 88 is depicted in FIG. 10 and is a cross-sectional view through Plane X of FIG. 11. Detachable panel assembly 88 incorporates at least one component panel 51 comprised of activatable, hardenable matrix 72 encapsulated within water impervious enclosure 70. Component panel 51 is itself encapsulated within a brushed nylon enclosure 76 with additional closed cell foam 78 providing cushioning to the skin-side interior surface of panel 88. A molded brace frame 90 is preferably recessed to accept the dimensions of detachable component panel assembly 88. A plurality of Velcro-type attachment pads 84, fastened to detachable panel assembly 88, are provided to removably secure each panel within the accepting recesses of molded brace frame 90 via Velcro-type receiving material 86 lining said recessed areas.

Detachable panel assembly 88 may be of a construction allowing easy removal and re-installation of component panel 51 within molded brace frame 90. In such a configuration, component panel 51 may have a structure similar to that illustrated in FIG. 9, and readily adapted to activation by means of immersion in water, rather than by water injection through inlet ports 40 accessed through port access hole 60.

An alternative embodiment of the present invention is illustrated in FIG. 11. A plurality of detachable panel assemblies 88 are shown recessed into molded brace frame 90, preferably constructed from closed cell foam. The initially pliable, detachable panel assemblies 88 are releasably installed into the recesses of molded brace frame 90, and secured therein by a plurality of Velcro-type attachment pads 84 and corresponding Velcro-type receiving material 86 lining the recessed areas. Rear component 34 is then positioned on the patient's back and preferably secured thereon by a plurality of Velcro-covered securing straps 36 extending circumferentially around the patient's torso, or to an apron arrangement at the front of the patient. When properly fitted, liquid is introduced into each detachable panel assembly 88 through at least one inlet port 40 externally accessible through port access hole 60. Upon completion of the chemical reaction, rear component 34 conforms to the unique configuration of the patient's back.

In one embodiment of the invention, as illustrated in FIG. 12, a single formable component of moderately complex geometry comprises the entirety of rear component 34. Shoulder protrusions 98, upper protrusions 94, and lower protrusions 95 comprise the main structural elements of rear component 34. A plurality of securing straps 96, 36, and 92 are employed to secure rear component 34 to the patient's back, or by using the apron type structure.

Shoulder straps 96, with one end fastened just above upper protrusions 94, run under each arm, extend over the front shoulder area, and pass through buckle loops 100 affixed to the end of each shoulder protrusion 98, preferably being secured by Velcro-type attachment and receiving material covering shoulder straps 96. Shoulder protrusions 98 generally extend toward the patient's shoulders from the main body of rear component 34. Upper protrusions 94 and lower protrusions 95 respectively extend symmetrically from the spinal region toward the sides of the torso. A plurality of securing straps 36 and waist strap 92 extend around the sides and front of the torso and are detachably coupled, optionally to the apron, by means of Velcro-type mating material covering said straps or other known securing arrangements. A plurality of inlet ports 40 are provided for introducing water to the activatable, hardenable material contained therein. An oval shaped cut-out 99, between upper and lower protrusions 94 and 95 respectively, allows for a minimum of spinal movement.

FIG. 13 is quite similar to the embodiment illustrated in FIG. 12, differing only in the configuration of shoulder protrusions 98. Individual shoulder protrusions 98 emanate from upper protrusions 94 extending generally toward the patient's shoulders. Shoulder protrusions 98 pictured in FIG. 13 provide a greater degree of flexibility and mobility of the upper shoulder and neck area, often required for patient's engaging in recuperative and rehabilitative procedures.

In another embodiment of the present invention, as illustrated in FIG. 14, rear component 34 is comprised of a single moldable rear component 102 which incorporates pneumatic pad 104. Alternatively, moldable rear component 102 may be comprised of a plurality of component panels 33 with resilient material 41 interposing adjacent panels 33 as shown in FIG. 3. Pneumatic pad 104 may be removably or permanently affixed to the interior surface of moldable rear component 102. Pneumatic pad 104 may be pre-inflated, and may include inflation and deflation means. Additional foam padding or other resilient material (not shown) may cover pneumatic pad 104 to provide additional comfort and durability. A plurality of securing straps 36 circumferentially extend around the torso and are secured to apron 120 by Velcro-type mating material covering said straps. A plurality of inlet ports 40 are provided on the exterior surface of moldable rear component 102 for introducing water to the encapsulated activatable, hardenable material.

Figure 15:
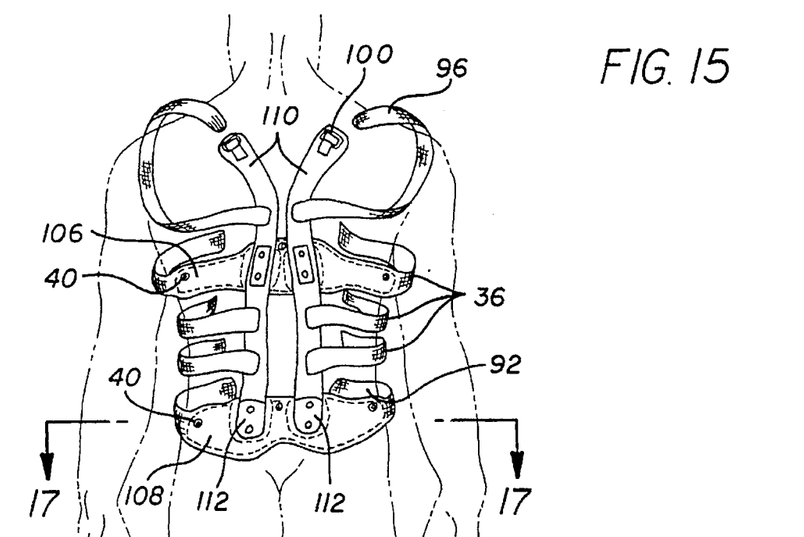
FIG. 15 illustrates yet another embodiment of the present invention.

As an alternative to the one-piece rear component 34 configuration illustrated in FIGS. 12 and 13, the embodiment shown in FIG. 15 incorporates hardenable upper and lower components 106 and 108 respectively mounted to a pair of semi-rigid support struts 110 generally extending along the patient's spine. Support struts 110 are preferably fashioned from malleable aluminum, but may be constructed from high-strength engineering plastics or other similar composites. Upper and lower components 106 and 108 are respectively mounted and secured to support struts 110 by at least one rivet fastener 130 through each strut mount site 112. Securing strap pairs 96, 36, and 92 respectively extend from support struts 110, circumferentially around the patient's torso, and are secured to apron 120 by means of Velcro-type mating material covering the opposing ends of said strap pairs. Inlet ports 40 are provided on the exterior surface of upper and lower components 106 and 108 through which liquid may be injected to activate the encapsulated hardenable material.

Figure 17:
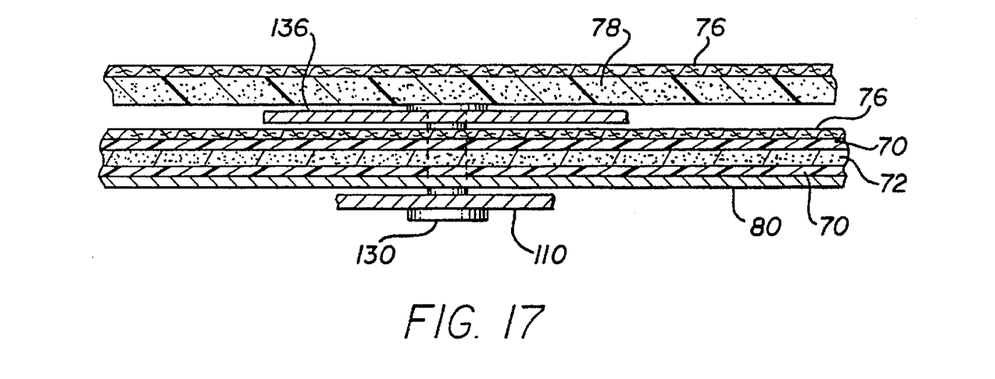
FIG. 17 is a cross-sectional view through Plain XVII of FIG. 15, with a detailed showing of a mounting means incorporated into the component's structure.

FIG. 17 shows a cross-sectional view through Plane XVII of lower component 108 pictured in FIG. 15. In particular, strut mount 112 is pictured with rivet 130 passing through support strut 110, hardenable matrix 72, and reinforcement plate 136. Reinforcement plate 136 may be constructed from high-strength plastic, aluminum, or other rigid material. Moreover, the width and thickness dimensions of reinforcement plate 136 may be the same as, or different from, those of support strut 110. Reinforcement plate 136 may be included to distribute the mechanical load through rivet 130 from the support strut 110, or may be excluded depending on the anticipated stress to strut mount 112. Closed cell foam layer 78 may be recessed to accommodate the thickness of the rivet end 130 and reinforcement plate 136.

Figure 16:
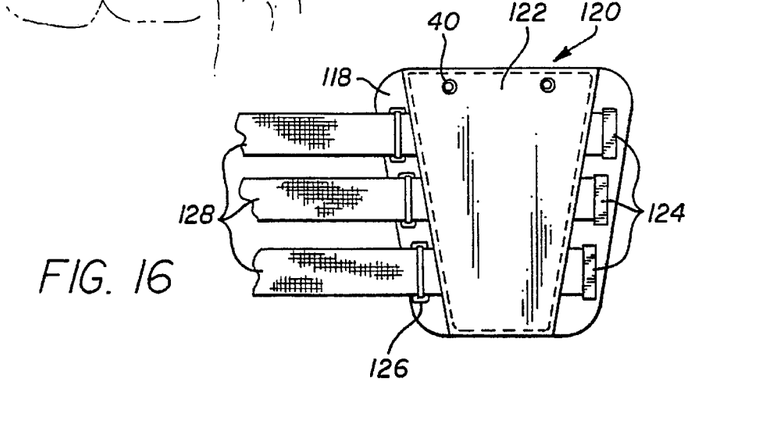
FIG. 16 illustrates a front apron member adaptable for use with several embodiments of the present invention.

FIG. 16 is a showing of front optional apron assembly 120 which may be employed together with several embodiments of the present invention as illustrated in FIGS. 11 through 15. In each of these figures, securing straps 36, extending from rear component 34 and circumferentially around the patient's torso, terminate on Velcro-type receiving straps 128 and Velcro-type receiving pads 124 on apron assembly 120. Instead of the use of Velcro pads 124, the ends of the straps may extend through D-rings and be secured by Velcro back on intermediate sections of the straps. Front apron assembly 120 is generally dimension to cover the middle chest and abdominal region of the front torso. Activatable, hardenable material is preferably contained within apron component 122, with at least one inlet port 40 provided as a conduit through which water or other liquid may be introduced to activate said hardenable material.

Alternatively, apron component 122 may be detachably affixed to front apron assembly 120 such that it may be easily removed, immersed in water to activate the pre-polymer matrix, re-installed into front apron assembly 120, and secured against the front torso by use of securing straps 36. Upon completion of the chemical reaction, apron component 122 hardens and conforms to the patient's mid-section of the front torso. A plurality of buckle loops 126 are mounted on front apron base 118, with apron base 118 optionally constructed from flexible plastic or other resilient material. Similarly, a plurality of Velcro-type receiving pads 124 may be mounted on front apron base 118 to receive securing straps 36 covered with mating Velcro-type material.

Figure 18:
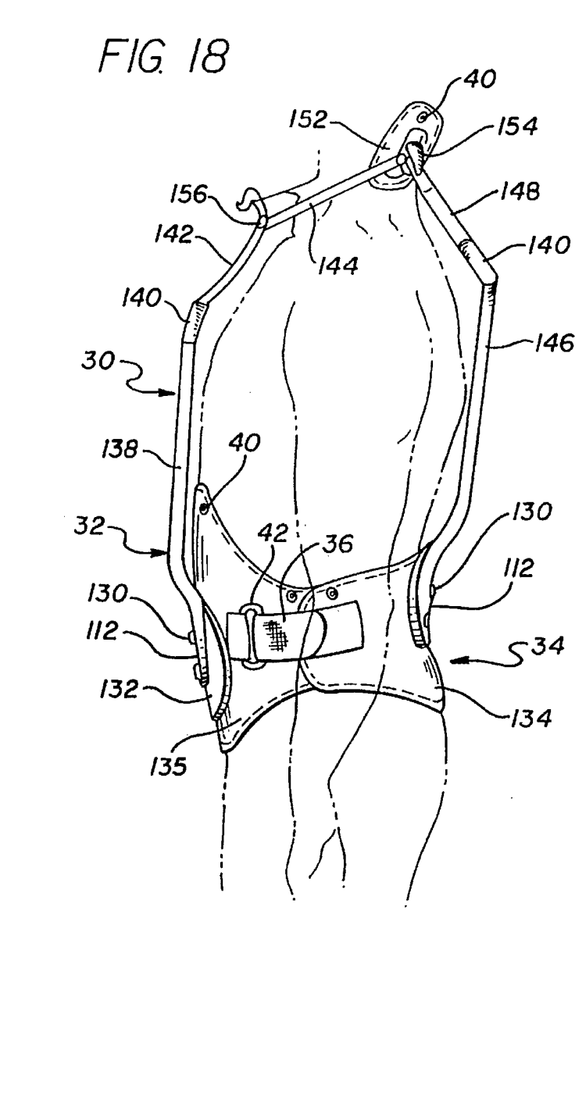
FIG. 18 is a side view of a formable back brace incorporating a means for isolating head and neck movement.

Turning now to FIG. 18, this figure provides a side view of an alternative embodiment of the present invention incorporating neck and head isolation members for patients having severe head and/or neck injuries. Front and rear components 32 and 34 are shown releasably coupled around the patient's lower torso and secured thereon by at least one pair of securing straps 36 passing through buckle loops 42. A plurality of inlet ports 40 are distributed over the exterior surfaces of front and rear components 32 and 34. The lower end of front strut 138 is mounted to front component 32 by a plurality of rivets 130 passing through front strut 138, front strut plate 32, and through hardenable matrix 72 and reinforcement plate 136 (not shown) integrated within front component 32, preferably in a manner similar to that illustrated in FIG. 17. Chin support 142 is coupled to front strut 138 at strut coupling 140. Jaw support members 144, on either side of the patient's head, extend from chin support attachment sites 156 to attachment couplings 154 mounted on rear skull components 152. Activatable, hardenable material may be included within each rear skull component 152, with at least one inlet port 40 provided to facilitate the introduction of water or other liquid into rear skull components 152.

A pair of rear struts 146 are mounted on rear component 34 and extend generally along the patient's spine toward the shoulders. Neck support members 148, each mounted to attachment couplings 154 fixed on rear skull components 152, are connected to each rear strut 146 by interposed strut couplings 140. Rear struts 146 are mounted to rear component 34 by a plurality of rivets 130 passing through strut mounts 112 and terminating within rear component 34 preferably in a manner similar to that depicted in FIG. 17.

Figure 19:
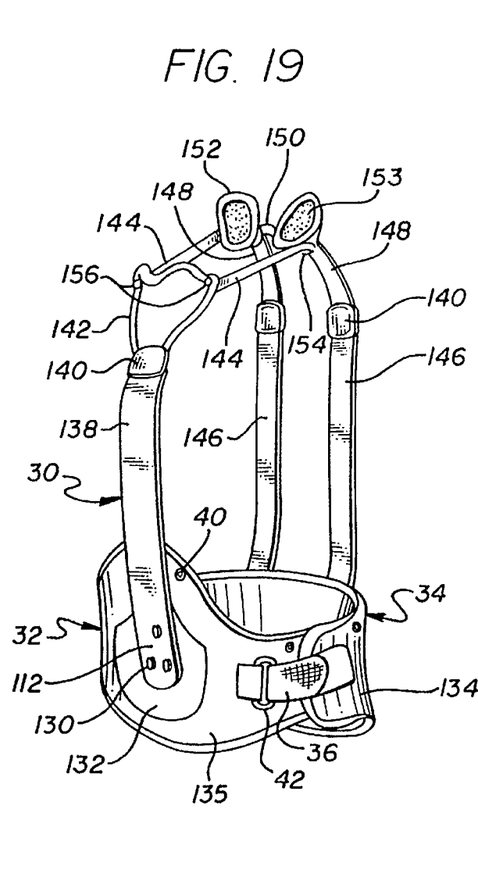
FIG. 19 is a full view of an embodiment of the invention incorporating a means for isolating head and neck movement.

FIG. 19 is a rotated view of FIG. 18 illustrating the pair of rear struts 146 extending from rear component 134, along the patient's spine to strut couplings 140, and connecting to neck support members 148 which in turn terminate at rear skull components 152. An additional layer of padding 153 may be included on each rear skull component 152 to provide additional comfort to the patient.

Figure 20:
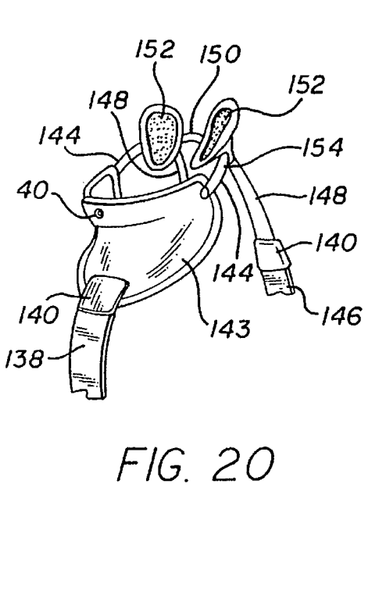
FIG. 20 illustrates an alternative embodiment of the head isolation means.

In an alternative embodiment, as illustrated in FIG. 20, chin support component 143 may be employed to substantially minimize head and neck movement. Activatable, hardenable material, contained within chin support component 143, may be activated by liquid introduced through at least one inlet port 40. Upon completion of the chemical reaction, chin support component 143 hardens and conforms to the unique configuration of the patient's chin and jaw. This embodiment of the present invention is most suited to patient's having severe head and/or neck injuries.

For completeness as to the description of the various materials and geometries employed in the construction of the hardenable component structures discussed hereinabove, reference is made to U.S. Pat. Nos. 4,928,678; 4,852,557; and 4,996,979. The materials and construction geometries disclosed in the three aforementioned U.S. patents are incorporated by reference with respect to the embodiments previously discussed above.

It is to be understood that the foregoing description of the accompanying drawings shall relate to preferred and illustrated embodiments of the invention. Other embodiments may be utilized without departing from the spirit and scope of the invention. Thus, by way of example and not of limitation, the number of securing straps may be varied from one to several. Also, materials other than those described may be employed to form hardenable components of differing constructions depending on application requirements. Various combinations of materials other than those described hereinabove may be employed to construct the hardenable components. Vinyl or other elastomer and/or fabric materials may be employed to form the durable exterior shell. Conventional attachment arrangements may be used in conjunction with the securing straps to secure the back brace components to the patient's torso. Moreover, the dimensions of front and rear components 32 and 34 may be varied to isolate specific portions of the patient's torso, or its entirety. Furthermore, pneumatic pad 104 may be integrated into front component 32 in combination with, or exclusive of, rear component 34. Various other materials, such as graphite, Kevlar and other fibrous material may comprise hardenable matrix 72 impregnated with a urethane prepolymer. Also, semi-rigid support members may be integrated into back brace 30, or may replace one or more component panels 33. Molded brace frame 90 may be constructed from engineering plastics or other high-strength materials rather than from closed cell foam. Concerning the combination of in-situ formable orthopaedic supports and air bladders, it is to be understood that this principle is applicable to orthopaedic devices other than back braces, such as ankle braces, short leg walkers, elbow supports and other orthopaedic devices whenever support and adjustable padding is desired; for example to accommodate variations in swelling.

Accordingly, it is to be understood that the detailed description and drawings set forth herein above are for illustrative purposes only and do not constitute a limitation on the scope of the invention.

What is claimed is:

1. A custom "in situ" formable back brace, comprising:
a back assembly;
said back assembly including (a) a water impervious sealed first enclosure containing a matrix impregnated with an activatable hardenable material and (b) a water impervious sealed second enclosure containing a matrix impregnated with an activatable hardenable material; and
a belt assembly for securing said first and second enclosures against the patient's back.

2. The brace of claim 1 wherein said back assembly includes a first fluid inlet port communicable with said first enclosure and a second fluid inlet port communicable with said second enclosure.

3. The brace of claim 1 wherein said first and second enclosures are vertically aligned relative to one another.

4. The brace of claim 1 wherein said back assembly includes resilient material interposed between said first and second enclosures to provide flexibility to said back assembly and custom fit around the patient's torso.

5. The brace of claim 1 wherein said first and second enclosures both comprise vertical panels.

6. The brace of claim 1 wherein said first and second enclosures are permanently integrated components of said back assembly.

7. The brace of claim 1 wherein said back assembly includes port means for injecting activating fluid into said first and second enclosures to cause, with said belt means holding said first and second enclosures against the patient's back, the activatable materials therein to harden and conform to the unique configurations of the patient's back.

8. The brace of claim 1 wherein said belt assembly includes first and second length-adjustable belts both attached to said back assembly and extendible across the front of the patient's torso, generally one above the other.

9. The brace of claim 1 wherein said back assembly includes a water impervious sealed third enclosure containing a matrix impregnated with an activatable hardenable material, said belt assembly holding said first, second and third enclosures in a side-by-side arrangement against the patient's back.

10. The brace of claim 1 wherein said back assembly is extendible around the front of the patient to encircle the patient's torso and held in position by said belt assembly.

11. The brace of claim 10 wherein said back assembly includes a water impervious sealed third enclosure containing a matrix impregnated hardenable material, said belt assembly holding said third enclosure against the front of the patient's torso.

12. The brace of claim 11 wherein said back assembly includes resilient material between said third and second enclosures.

13. The brace of claim 1 wherein said belt assembly includes a chest belt positionable across the patient's chest and a waist belt positionable across the patient's waist.

14. The brace of claim 1 wherein at least a portion of said first enclosure is adjacent to a thoracic part of the patient's back.

15. A custom "in situ" formable back brace, comprising:
a back assembly including a water impervious sealed enclosure containing a matrix impregnated with an activatable hardenable material;
said back assembly being positionable in an operative position against a patient's back;
at least one belt securing said back assembly in the operative position; and
said enclosure, with said back assembly in the operative position, extends up from the patient's waist to the thoracic region of the patient just below the shoulders.

16. The back brace of claim 15 wherein said at least one belt includes patient waist and chest belts.

17. The back brace of claim 15 wherein said back assembly includes a fluid inlet port at the top of said enclosure at an exterior surface thereof.

18. A custom "in situ" formable back brace, comprising:
a brace frame securable in an operative position against a patient's back, said back frame having an inward surface;
a panel assembly securable to said inward surface in a secured position and unsecurable therefrom;
said panel assembly including a water impervious sealed enclosure containing a matrix impregnated with an activatable hardenable material; and
with said brace frame in the operative position, said material can be fluid activated to cause said material to harden and conform to the unique shape of the patient's adjacent back.

19. The back brace of claim 18 wherein said panel assembly includes a fluid injection port for injecting an activating fluid to activate the material.

20. The back brace of claim 19 wherein said brace frame includes an opening in alignment with said fluid injection port with said panel assembly in the secured position.

21. The back brace of claim 18 further comprising hook-and-loop securing means for releasably securing said panel to said inward surface.

22. The back brace of claim 18 wherein said brace frame includes on said inward surface a recess dimensioned to receive therein said panel assembly in the secured position.

23. The back brace of claim 18 further comprising a patient chest belt and a waist belt attached to said brace frame.

24. The back brace of claim 18 wherein said panel assembly defines a first panel assembly, and further comprising second and third panel assemblies securable to said inward surface on opposite sides of said first panel assembly.

25. A custom "in situ" formable back brace, comprising:

a back assembly adapted to wrap around a patient's torso, and having a front torso portion and a back torso portion;

said back assembly including a water impervious sealed first enclosure containing a matrix impregnated with an activatable hardenable material and a water impervious sealed second enclosure containing a matrix impregnated with an activatable hardenable material;

said first enclosure is at said front torso portion and said second enclosure is at said back torso portion; and a belt assembly for securing said back assembly around the patient's torso.

26. The back brace of claim 25 wherein said back assembly includes a first fluid injection port communicable with said first enclosure and a second fluid injection port communicable with said second enclosure.

27. The back brace of claim 25 wherein said belt assembly includes a length-adjustable chest belt and a length-adjustable waist belt.

28. The back brace of claim 25 wherein said back assembly includes resilient material between said first and second enclosures.

29. The back brace of claim 25 wherein said first and second enclosures extend up to the thoracic areas of the patient with said belt assembly securing said back assembly around the patient's torso.

30. The back brace of claim 25 wherein said back assembly includes lateral ends of said rear torso portion overlapping lateral ends of said front torso portion.

31. A custom "in situ" formable back brace, comprising:

a brushed nylon layer positionable against a patient's body portion;

a first cushioning foam layer adjacent said nylon layer;

fluid-activatable, hardenable material which is encapsulated within a water impervious enclosure and which remains initially pliable until activating fluid is introduced to cause said material to harden and conform to the unique shape of the patient's adjacent body portion;

a second cushioning foam layer on a side of said enclosure opposite to that of said first cushioning foam layer; and an exterior shell covering said second cushioning foam layer.

32. The back brace of claim 31 wherein said enclosure is disposed between said first and second cushioning foam layers.

33. A support brace assembly, comprising:

a supporting belt brace adapted to encircle and to be secured relative to a patient's lower torso, said belt brace having an inward surface and through-opening through said inward surface;

a pouch on said inward surface;

a component pad containing a matrix impregnated with an activatable hardenable material, said pad being insertable into said pouch in an operative position with said fluid port operatively accessible, with said supporting belt secured around the lower torso, via said through-opening such that the activating fluid can be injected into said pad to cause the material therein to harden and conform to the unique shape of the patient's adjacent lower back region; and securing tabs attached to said inward surface and releasably securing said pad in the operative position.

34. A custom "in situ" formable back brace assembly, comprising:

a back brace positionable against the patient's back;

a shoulder strap, a chest strap, and a waist strap, each attached to said back brace; and a water impervious sealed enclosure containing a matrix impregnated with an activatable hardenable material supported by said back brace.

35. The back brace assembly of claim 34 wherein said back brace includes spaced upper and lower components and a pair of support struts mounted to said upper and lower components.

36. The back brace assembly of claim 35 wherein said support struts are mounted to said upper and lower components with rivets.

37. The back brace assembly of claim 34 wherein said enclosure defines a lower right enclosure, and further comprising lower left, upper right and lower right enclosures, each supported by said back brace and thereby positionable against respective portions of the patient's back, and each containing a matrix impregnated with an activatable hardenable material.

38. The back brace assembly of claim 34 wherein said back brace includes a central vertical cut-out area corresponding to the patient's spinal area.

39. The back brace assembly of claim 34 wherein said back brace includes shoulder protrusions to which said shoulder strap is secured, upper protrusions to which said chest strap is secured and lower protrusions to which said waist strap is secured.

40. The back brace assembly of claim 39 further comprising mid-torso securing straps attached to said back brace between said upper and lower protrusions.

41. A custom "in situ" formable brace assembly, comprising:

a front apron dimensioned to generally cover the middle chest and abdominal region of the front torso of a patient;

at least one torso strap attached to said front apron and extendible about the patient's torso; and a water impervious sealed enclosure containing a matrix impregnated with an activatable hardenable material and supported by said front apron to thereby be positioned adjacent to the patient's front torso.

42. The brace assembly of claim 41 wherein said material in said enclosure is fluid activated through an injection port and with said enclosure supported by said front apron.

43. The brace assembly of claim 41 wherein said material in said enclosure is fluid activated and subsequently said enclosure is attached to said front apron.

44. A custom "in situ" formable bracing assembly, comprising:

a rear back brace component;

a front apron;

at least one securing strap interconnecting said rear back brace and said front apron around a patient's torso; and fluid-activatable hardenable material contained in an enclosure held in said front apron.

45. The bracing assembly of claim 44 wherein said from apron when positioned with said securing strap on the patient, is generally dimensioned to cover the middle chest and abdominal region of the patient's front torso.

46. The bracing assembly of claim 44 wherein said front apron includes an activating-fluid inlet port communicating with said hardenable material.

47. The bracing assembly of claim 44 further comprising fluid-activatable hardenable material contained in said rear back brace component.

48. A head and neck brace assembly, comprising:

a chin support;

a jaw support member connected to said chin support;

a rear skull component connected to said jaw support member;

interconnected front and rear lower torso components;

a front strut connecting said chin support to said front torso component; and a rear strut connecting said rear skull component to said rear torso component;

wherein said rear skull component includes fluid-activatable hardenable material, hardenable to conform to a patient's adjacent rear skull area.

49. A head and neck brace assembly, comprising:

a chin support;

a jaw support member connected to said chin support;

a rear skull component connected to said jaw support member;

interconnected front and rear lower torso components;

a front strut connecting said chin support to said front torso component; and a rear strut connecting said rear skull component to said rear torso component;

wherein said front torso component includes fluid-activatable hardenable material, hardenable to conform to a patient's adjacent front torso area.

50. A head and neck brace assembly, comprising:

a chin support;

a jaw support member connected to said chin support;

a rear skull component connected to said jaw support member;

interconnected front and rear lower torso components;

a front strut connecting said chin support to said front torso component; and a rear strut connecting said rear skull component to said rear torso component;

wherein said rear torso component includes fluid-activatable hardenable material, hardenable to conform to a patient's adjacent rear torso area.

51. A head and neck brace assembly, comprising:

a chin support;

a jaw support member connected to said chin support;

a rear skull component connected to said jaw support member;

interconnected front and rear lower torso components;

a front strut connecting said chin support to said front torso component; and a rear strut connecting said rear skull component to said rear torso component;

wherein said chin support includes fluid-activatable hardenable material, hardenable to conform to a patient's adjacent chin area.

* * * * *